US010722451B2

(12) United States Patent
Royer

(10) Patent No.: US 10,722,451 B2
(45) Date of Patent: Jul. 28, 2020

(54) TREE BARK EXTRACT AS ANTI-AGING COMPOSITION AND USES THEREOF

(71) Applicant: LES LABORATOIRES BIOFOREXTRA, Levis (CA)

(72) Inventor: Mariana Royer, Levis (CA)

(73) Assignee: LES LABORATORIES BIOFOREXTRA (CA)

( * ) Notice: Subject to any disclaimer, the term of this patent is extended or adjusted under 35 U.S.C. 154(b) by 204 days.

(21) Appl. No.: 15/674,681

(22) Filed: Aug. 11, 2017

(65) Prior Publication Data

US 2019/0046432 A1    Feb. 14, 2019

(51) Int. Cl.
| A61K 8/9789 | (2017.01) |
| A61K 8/34 | (2006.01) |
| A61K 8/9767 | (2017.01) |
| A61Q 19/08 | (2006.01) |

(52) U.S. Cl.
CPC ............ *A61K 8/9789* (2017.08); *A61K 8/345* (2013.01); *A61K 8/9767* (2017.08); *A61Q 19/08* (2013.01)

(58) Field of Classification Search
None
See application file for complete search history.

(56) References Cited

U.S. PATENT DOCUMENTS 8,431,170 B2   4/2013  Ahlnäs
8,906,957 B2   12/2014 Steffan et al.

FOREIGN PATENT DOCUMENTS

| FR | 2915093 A1 | 10/2008 |
| SI | 22882 A | 10/2010 |
| WO | 2006113700 A1 | 11/2006 |
| WO | 2012021981 A1 | 2/2012 |
| WO | 2012021983 A1 | 2/2012 |
| WO | 2012055010 A1 | 5/2012 |

OTHER PUBLICATIONS 2019 http://longevity.about.conn/od/researchandnnedicine/p/age radicals.htnn?p=1.*
Sastre et al., the Role of Mitochondrial Oxidative Stress in Aging, 2003, Free Radic Biol Med, 35: 1-8.*
2019 http://dernnatology.about.conn/cs/beauty/a/suneffect.htnn?p=1.*
Boucher et al. Jun., 2017, Acer rubrum Bark Extract, the new Natural and Eco-responsible Anti-ageing IngredientObtained from a Coproduct of the Canadian Forest Industry, Chapter Ii, Global Ingredients & Formulations Guide 2017, Sofw Verlag Fur chemische industrie, H. Ziolkowsky GmbH, Thannhausen.*
Royer, Mariana et al. "Polyphenol contents and radical scavenging capacities of red maple (*Acer rubrum* L.) extracts" Food and Chemical Toxicology 49 (2011), pp. 2180-2188.
Garcìa-Pérez, Martha-Estelle et al. "Picea mariana bark : A new source of trans-resveratrol and other bioactive polyphenols" Food Chemistry 135 (2012) pp. 1173-1182.
Garcìa-Pérez, Martha-Estelle et al. "Antioxidant, toxicological and antiproliferative properties of Canadian polyphenolic extracts on normal and psoriatic keratinocytes" Journal of Ethnopharmacology 132 (2010) pp. 251-258.
Yuan, Tao et al. "New maplexins F-I and phenolic glycosides from red maple (*Acer rubrum*) bark" Tetrahedron 68 (2012) pp. 959-964.
Legault, Jean et al. "Antioxidant Potential of Bark Extracts from Boreal Forest Conifers" Antioxidants (Bael) Sep. 2013; 2(3), pp. 77-89.
Royer, Mariana et al. "Study of netraceutical, nutricosmetics and cosmeceutical potentials of polyphenolic bark extracts from Canadian forest species" PharmaNutrition 1 (2013) pp. 158-167.
O'Brien, J., Wilson, I.H., Orton, T.C., & Pognan, F. 2000. Investigation of the Alamar Blue (resazurin) fluorescent dye for the assessment of mammalian cell cytotoxicity. European journal of biochemistry, 267 17, 5421-6.
Moure, A., Cruz, J.M., Franco, D., Manuel Dominguez J., Sineiro, J., Dominguez, H., Nunez, M.J., Carlos Parajo, J., 2001. Natural antioxidants from residual sources. Food Chem. 72, 145-171.
Stevanovic, T., Diouf, P.N., Garcia-Perez, M.-E., 2009. Bioactive polyphenols from healthy foods and forest biomass. Curr. Nutr. Food Sci. 5, 264-295.
Gupta, D, 2013. UV Absorbing Properties of Some Plant Derived Extracts. Research Journal of Chemical and Environmental Sciences, vol. 1, Issue 2 (Jun. 2013): 34-36.

* cited by examiner

*Primary Examiner* — Terry A Mckelvey
*Assistant Examiner* — Catheryne Chen
(74) *Attorney, Agent, or Firm* — Lavery, De Billy, LLP; Julie Gauvreau

(57) ABSTRACT

The present invention provides a crude extract from the bark of an *Acer rubrum* (AR) tree and/or *Picea mariana* (PM), method of preparation and its use for inhibiting the signs of skin aging (such as wrinkles and/or dehydration) caused by at least one of: increased elastase activity, increased collagenase activity, decreased elastin synthesis, decreased collagen synthesis or decreased involucrin synthesis, in skin fibroblast cells, particularly those of a human subject.

20 Claims, 12 Drawing Sheets

Grey: growth 24 hrs    black: growth 48 hrs

Grey: growth 24 hrs    black: growth 48 hrs

*Figure 3*
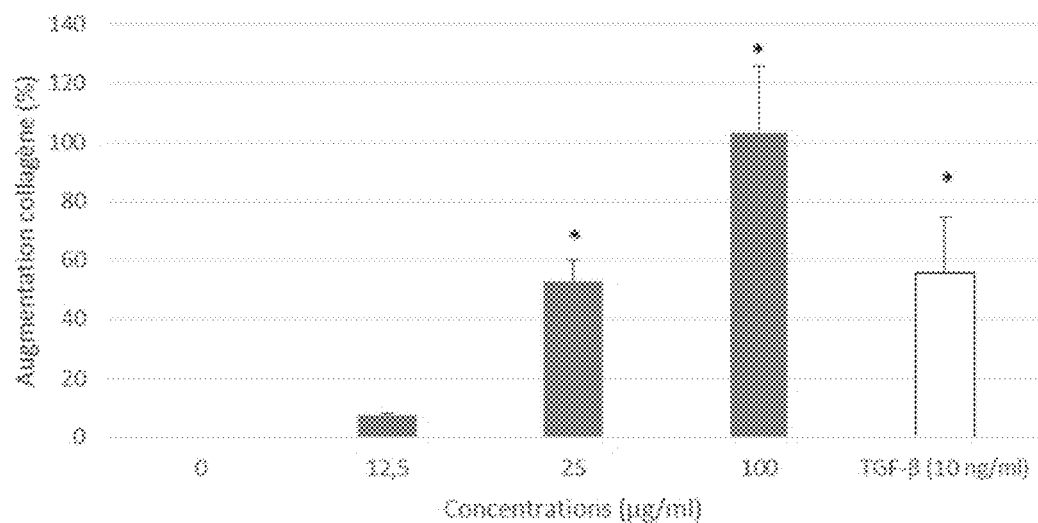
*Figure 4A*  *Figure 4B*  *Figure 4C*
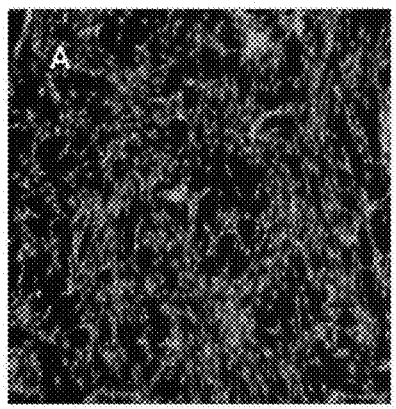 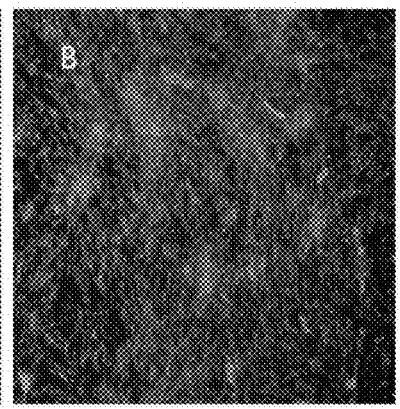 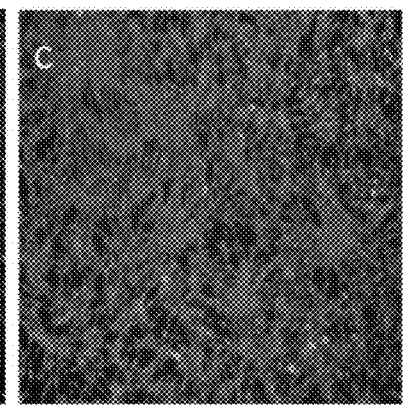

Grey: growth 24 hrs     black: growth 48 hrs

Grey: growth 24 hrs     black: growth 48 hrs

Figure 8A
Figure 8B
Figure 8C
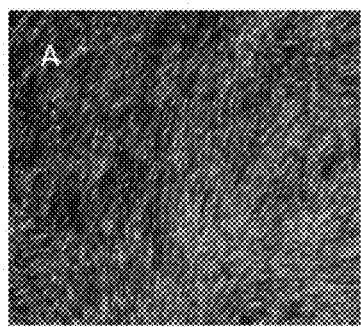
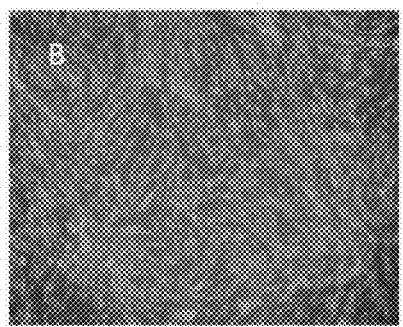
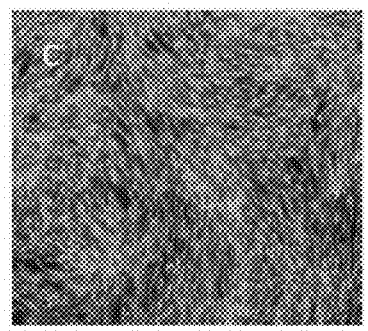
Figure 9
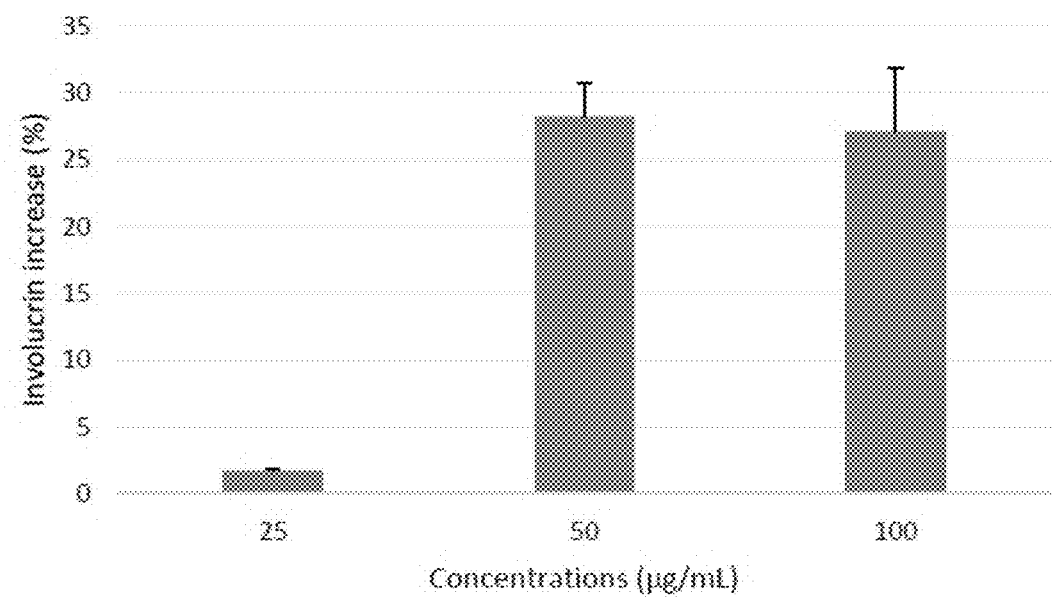

left: growth 24 hrs    right: growth 48 hrs left: growth 24 hrs    right: growth 48 hrs

*Figure 12*
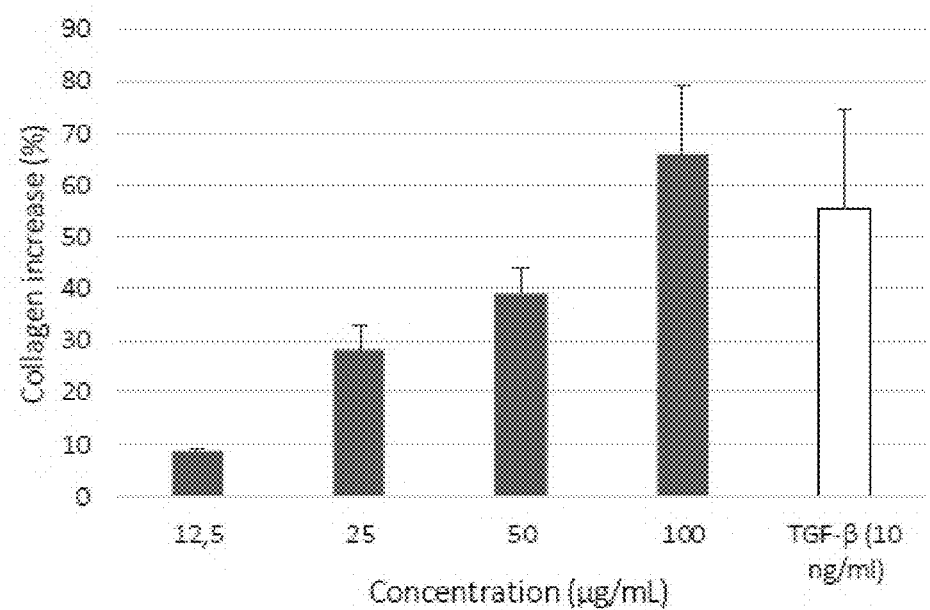
*Figure 13A*  *Figure 13B*  *Figure 13C*
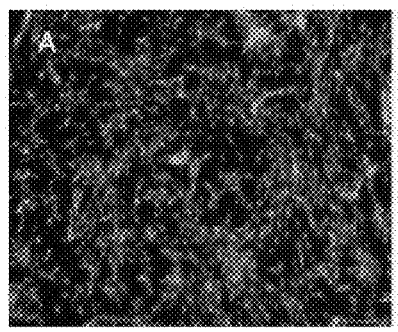 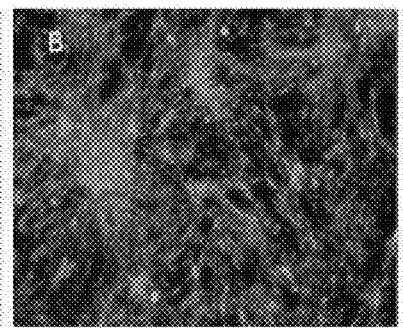 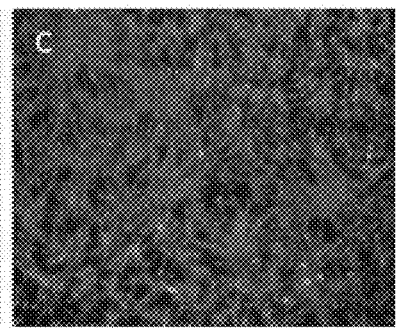

Left: growth 24 hrs    Right: growth 48 hrs

Left: growth 24 hrs    Right: growth 48 hrs

Figure 15
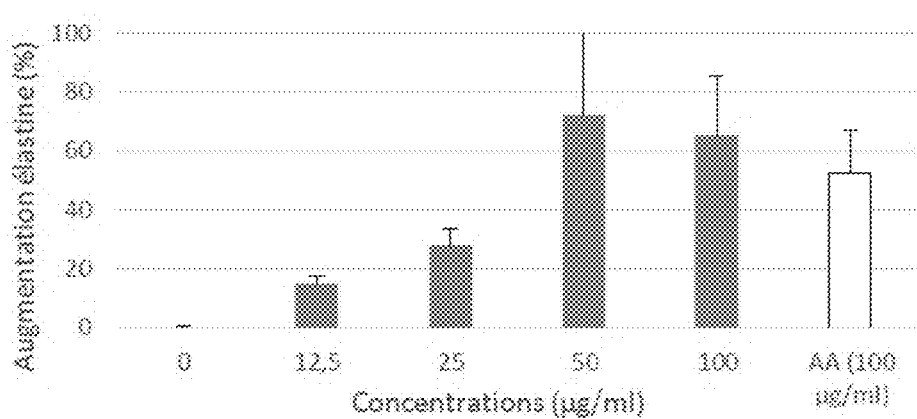
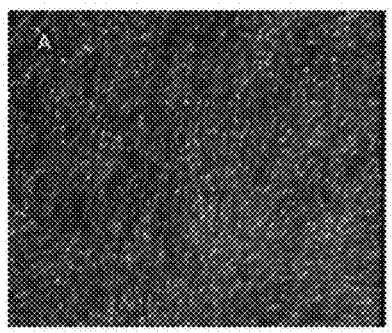
Figure 16A
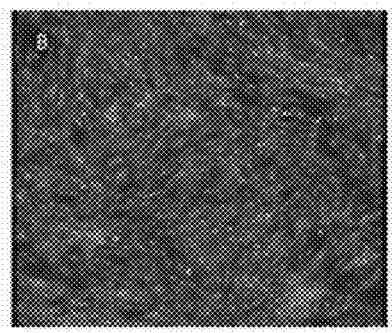
Figure 16B
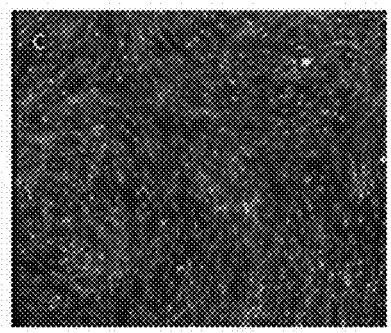
Figure 16C

TREE BARK EXTRACT AS ANTI-AGING COMPOSITION AND USES THEREOF

FIELD OF THE INVENTION

The present invention relates to extracts from the bark from *Acer rubrum* (AR) or *Picea mariana* (PM), compositions comprising one or both extracts, method of preparation and use for inhibiting the enzymes causing aging of skin fibroblast cells.

BACKGROUND OF THE INVENTION

Finding new natural, safe and economical antioxidant substances, especially from abundant and low-value raw materials is a real challenge nowadays, especially in an effort to develop the sustainability concept (Moure et al., 2001). Some industries, such as those related to food additive production, pharmaceutics and cosmetics have increased their efforts in obtaining bioactive compounds from natural products by extraction and purification. Forest biomass contains the same bioactive molecules as the fruits and vegetables considered as healthy diets (Stevanovic et al., 2009) and the residues of industrial wood transformation, available in huge quantities, represent therefore an abundant and inexpensive source of bioactive molecules.

Extractives obtained from the bark of red maple and/or black spruce considered as forest industry residues, can be advantageously utilised as sources of potent antioxidants. The results of this study show that red maple stem bark and to a lesser extent the bark of branches extracts can constitute potential sources of new antioxidant agents, rich in polyphenols. Since the stem bark represents the most important residue of red maple and black spruce wood transformation and is available in high quantities, the implementation of an extraction procedure in the existing wood processing industries could represent a viable solution to add value to the existing transformations of this wood species.

The extracts of red maple bark and/or black spruce bark have now been found to have specific anti-elastase and anti-collagenase activities that make it an anti-aging agent when used as a cosmetic.

SUMMARY OF THE INVENTION

A main aspect intended to be addressed by the present invention is to provide a novel extract from the bark of *Acer rubrum* (Red maple).

A main aspect intended to be addressed by the present invention is to provide a novel extract from the bark of *Picea mariana* (Black spruce).

According to a further aspect, the present invention provides a composition comprising the extract as defined herein, in admixture with a physiologically acceptable excipient.

According to a further aspect, the present invention provides a composition comprising: an *Acer rubrum* (Red maple) bark extract, mixed with a *Picea mariana* (Black spruce) bark extract, in admixture with a physiologically acceptable excipient.

According to a further aspect, the present invention provides an anti-aging composition comprising an anti-enzyme effective amount of the extract as defined herein, or of the composition as defined herein, in admixture with a physiologically-acceptable excipient, wherein the enzyme is selected from: elastase and collagenase.

According to a further aspect, the present invention provides an anti-aging composition comprising a pro-synthesis effective amount of the extract as defined herein, or of the composition as defined herein, in admixture with a physiologically-acceptable excipient, wherein the synthesis is selected from: elastin, collagen and involucrin.

According to a further aspect, the present invention provides an extract or a composition comprising the extract as defined herein, for use as an anti-aging agent on skin cells.

According to a further aspect, the present invention provides a method for inhibiting an enzyme contacting a skin cell with an enzyme-inhibiting concentration of the extract or the composition as defined herein.

According to a further aspect, the present invention provides a method for preventing aging of a skin in a mammal comprising administering an enzyme-inhibiting concentration of the composition as defined herein to skin of the mammal.

According to a further aspect of the present invention, there is provided use of the extract as defined herein for inhibiting an enzyme of a skin cell.

According to a further aspect of the present invention, there is provided use of the extract as defined herein for the manufacture of composition for preventing aging of skin cells in a mammal.

According to a further aspect, the present invention provides use of the composition as defined herein for the prevention of skin aging in a mammal.

According to a further aspect, the present invention provides a method for inhibiting or preventing skin aging in a mammal, comprising contacting said skin with an enzyme-inhibiting concentration of a solvent extract from *Acer rubrum* tree bark or from *Picea mariana* tree bark, wherein the enzyme is selected from: elastase and collagenase.

According to a further aspect, the present invention provides a method of treating or preventing skin aging in a mammal, comprising contacting said skin with a synthesis-enhancing amount of a red maple bark solvent extract, wherein the synthesis is selected from: elastin, collagen and involucrin.

DETAILED DESCRIPTION OF THE INVENTION

Description of the Figures

FIG. 3. Effect of Red maple bark extract on collagen production. Skin fibroblasts were incubated both with and without the presence of increasing concentrations of the extract. The cells were then fixed and incubated with an antibody against type 1 collagen. The cell nuclei are also labeled with DAPI method. The results are expressed as a percentage of the collagen increase comparatively to untreated cells. TGF-β was used as a positive control. The data is significantly different from untreated cells; P<0.05; Wilcoxon signed Rank Test (SigmaStat™ 3.5).

FIG. 4A. Red maple bark extract's effect on collagen stimulation. Skin fibroblasts were incubated in absence of 100 μg/mL of the extract. The cells were then fixed and incubated with an antibody against type 1 collagen. The cell nuclei were also labeled with DAPI.

FIG. 4B. Red maple bark extract's effect on collagen stimulation. Skin fibroblasts were incubated in presence of 100 μg/mL of the extract. The cells were then fixed and incubated with an antibody against type 1 collagen. The cell nuclei were also labeled with DAPI.

FIG. 4C. Red maple bark extract's effect on collagen stimulation. Skin fibroblasts were incubated in presence TGF-β (10 ng/ml) as a positive control. The cells were then fixed and incubated with an antibody against type 1 collagen. The cell nuclei were also labeled with DAPI.

FIG. 8A. Effect of Red maple bark extract on elastin stimulation. Skin fibroblasts were incubated 48 h in absence of 100 μg/mL of the extract. The cells were then fixed and incubated with an antibody against elastin. The cell nuclei were also labeled with DAPI.

FIG. 8B. Effect of Red maple bark extract on elastin stimulation. Skin fibroblasts were incubated 48 h in presence of 100 μg/mL of the extract. The cells were then fixed and incubated with an antibody against elastin. The cell nuclei were also labeled with DAPI.

FIG. 8C. Effect of Red maple bark extract on elastin stimulation. Skin fibroblasts were incubated 48 h in ascorbic acid 100 μg/mL (AA) as a positive control. The cells were then fixed and incubated with an antibody against elastin. The cell nuclei were also labeled with DAPI.

FIG. 9. Effect of Red maple bark extract on involucrin stimulation. Skin keratinocytes were incubated with and without the presence of increasing concentrations of Red maple bark extract. The cells were then fixed and incubated with an antibody against the involucrin. The cell nuclei were also labeled with DAPI. The results are expressed as a percentage of the involucrin increase compared with untreated cells. Data is significantly different from untreated cells; P<0.05; Wilcoxon signed Rank Test (SigmaStat™ 3.5).

FIG. 12. Effect of Black spruce bark extract on collagen production. Skin fibroblasts were incubated both with and without the presence of increasing concentrations of the extract. The cells were then fixed and incubated with an antibody against type 1 collagen. The cell nuclei are also labeled with DAPI method. The results are expressed as a percentage of the collagen increase comparatively to untreated cells. TGF-β was used as a positive control. The data is significantly different from untreated cells; P<0.05; Wilcoxon signed Rank Test (SigmaStat™ 3.5).

FIG. 13A. Black spruce bark extract's effect on collagen stimulation. Skin fibroblasts were incubated in absence of 100 μg/mL of the extract. The cells were then fixed and incubated with an antibody against type 1 collagen.

FIG. 13B. Black spruce bark extract's effect on collagen stimulation. Skin fibroblasts were incubated in presence of 100 μg/mL of the extract. The cells were then fixed and incubated with an antibody against type 1 collagen.

FIG. 13C. Black spruce bark extract's effect on collagen stimulation. Skin fibroblasts were incubated with TGF-β (10 ng/ml) as a positive control. The cell nuclei were also labeled with DAPI.

FIG. 16A. Effect of Black spruce bark extract on elastin stimulation. Skin fibroblasts were incubated 48 h in absence of the extract. The cells were then fixed and incubated with an antibody against elastin. The cell nuclei were also labeled with DAPI.

FIG. 16B. Effect of Black spruce bark extract on elastin stimulation. Skin fibroblasts were incubated 48 h in presence of 100 μg of the extract. The cells were then fixed and incubated with an antibody against elastin. The cell nuclei were also labeled with DAPI.

FIG. 16C. Effect of Black spruce bark extract on elastin stimulation. Skin fibroblasts were incubated 48 h in presence of Ascorbic acid (AA) as a positive control. The cells were then fixed and incubated with an antibody against elastin. The cell nuclei were also labeled with DAPI.

ABBREVIATIONS AND DEFINITIONS

Abbreviations

Figure 1:
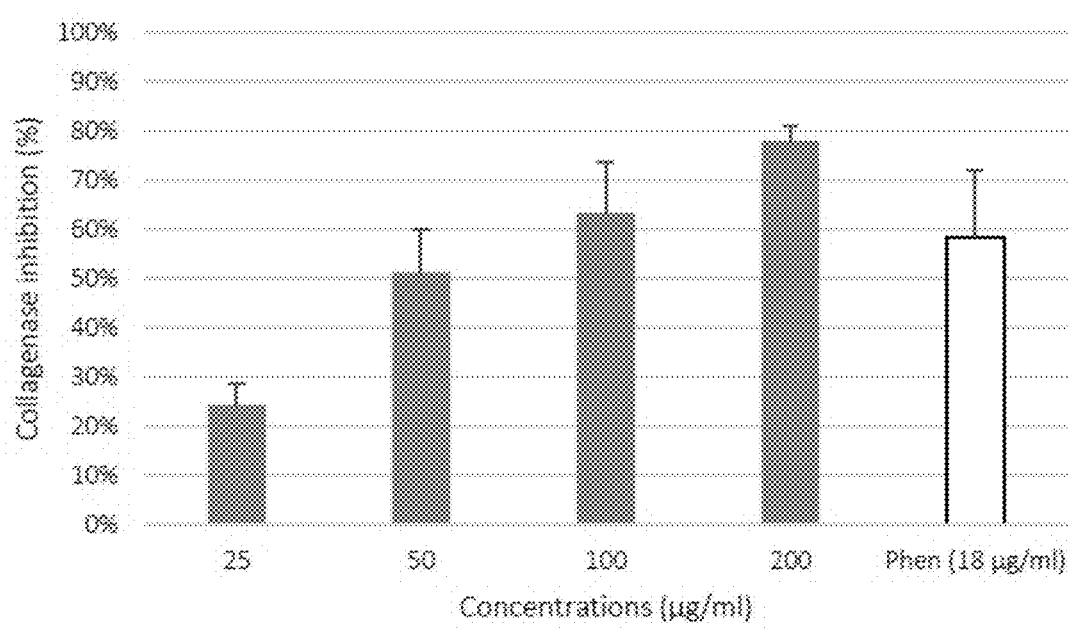
FIG. 1. Collagenase inhibition by Red maple bark extract. The collagenase was incubated both with and without the presence of increasing concentrations of the extract. The results are expressed as a percentage of the collagenase activity inhibition compared with the enzyme only. The 1,10-phenanthroline was used as a positive control. The data is significantly different from enzyme+substrate only; $P<0.05$; Wilcoxon signed Rank Test (SigmaStat™ 3.5).

AR: *Acer rubrum* or red Maple tree; PM: *Picea mariana* or Black spruce tree.

Definitions

The term "about" as used herein refers to a margin of + or −10% of the number indicated. For sake of precision, the term about when used in conjunction with, for example: 90% means 90%+/−9% i.e. from 81% to 99%. More precisely, the term about refer to + or −5% of the number indicated, where for example: 90% means 90%+/−4.5% i.e. from 86.5% to 94.5%.

As used herein the singular forms "a", "and", and "the" include plural referents unless the context clearly dictates otherwise. Thus, for example, reference to "a cell" includes a plurality of such cells and reference to "the culture" includes reference to one or more cultures and equivalents thereof known to those skilled in the art, and so forth. All technical and scientific terms used herein have the same meaning as commonly understood to one of ordinary skill in the art to which this invention belongs unless clearly indicated otherwise.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, un-recited elements or method steps.

As used herein, the terms "disease" and "disorder" may be used interchangeably or may be different in that the particular malady or condition may not have a known causative agent (so that etiology has not yet been worked out) and it is therefore not yet recognized as a disease but only as an undesirable condition or syndrome, wherein a more or less specific set of symptoms have been identified by clinicians.

"Mammal" includes humans and both domestic animals such as laboratory animals and household pets, (e.g. cats, dogs, swine, cattle, sheep, goats, horses, rabbits), and non-domestic animals such as wildlife and the like.

The term "subject" as used herein refers to an animal, preferably a mammal, and most preferably a human who is the object of treatment (prophylactic or therapeutic), observation or experiment.

The term "extract" as used herein means a composition prepared by contacting solvent with tree bark material, produced following the procedures of the invention, which demonstrates inhibitory activity against one or more cellular enzyme in vitro. In one aspect of the invention, an extract demonstrates inhibitory activity against skin cell elastase, collagenase or involucrine in vivo. As used herein, the term "extract" means an extract that is: crude, fractionated, sub-fractionated, separated, isolated, enriched or purified without being limited thereto.

The term "isolated" is used herein to indicate that the protein exists in a physical milieu distinct from that in which it occurs in nature. For example, the isolated molecule may be substantially isolated (for example enriched or purified) with respect to the complex cellular milieu in which it naturally occurs, such as in a crude/primary extract or secondary fractions. When the isolated molecule is enriched or purified, the absolute level of purity is not critical and those skilled in the art can readily determine appropriate levels of purity according to the use to which the material is to be put. In some circumstances, the isolated molecule forms part of a composition (for example a more or less crude extract containing many other substances) or buffer system, which may for example contain other components. In other circumstances, the isolated molecule may be purified to essential homogeneity, for example as determined spectrophotometrically, by NMR or by chromatography (for example LC-MS).

The term "primary" or "crude" means compounds or molecules that have not been entirely separated from the components of the original composition in which it was present. Therefore, the terms "separating", "purifying" or "isolating" refers to methods by which one or more components of the biological sample are removed from one or more other components of the sample.

The extracts described herein can be formulated as "compositions" by admixing them with additives such as physiologically-acceptable excipients, physiologically-acceptable carriers, and physiologically-acceptable vehicles, or as cosmetic formulations with additives such as pharmaceutically- and/or dermatologically-acceptable excipients, carriers, and/or vehicles.

As used herein, the term "dermatologically-acceptable" refers to molecular entities and compositions that are physiologically tolerable when applied topically on the skin and do not typically produce an allergic or similar unwanted reaction, such as redness or swelling and the like, when administered to human. Preferably, as used herein, the term "cosmetically acceptable" means approved by regulatory agency of the federal or state government or listed in the U.S. Pharmacopeia or other generally recognized pharmacopeia for use in animals, and more particularly in humans.

The term "carrier" refers to a diluent, adjuvant, excipient, or vehicle with which the compounds of the present invention may be administered. Sterile water or aqueous saline solutions and aqueous dextrose and glycerol solutions may be employed as carrier, particularly for topical formulations. Suitable cosmetically carriers are described in "Remington's Pharmaceutical Sciences" by E. W. Martin.

DETAILED DESCRIPTION OF PARTICULAR ASPECTS OF THE INVENTION

Solvent Extracts

With the aim of providing an alternative source of anti-aging extract, there is provided a crude aqueous solvent extract from the tree bark of: *Acer rubrum* (AR) or *Picea mariana* (PM). Particularly, the crude extract is an organic or inorganic solvent extract. More particularly, the extract's solvent is water or alcohol; and even more particularly: water or aqueous ethanol.

Particularly, the crude extract is any extract ranging from a 100% water to a 100% ethanol extract. Still, particularly, the crude extract is a 50% water: 50% ethanol extract of PM. Still, more particularly the crude extract is a 100% water extract of AR.

According to an alternative embodiment, there is provided a composition comprising a mixture of crude solvent extracts from the tree bark of: *Acer rubrum* (AR) and *Picea mariana* (PM).

Extract Form

In accordance with a particular aspect of the present invention, the extract is in dried form or in solution.

Composition and/or Formulation

In accordance with a particular aspect of the invention, there is provided a composition comprising the AR extract as defined herein, in admixture with a physiologically—(i.e. pharmaceutically or dermatologically) acceptable carrier.

In accordance with a particular aspect of the invention, there is provided a composition comprising the PM extract as defined herein, in admixture with a physiologically—(i.e. pharmaceutically or dermatologically) acceptable carrier.

In accordance with a particular aspect of the invention, there is provided a composition comprising the AR extract admixed with the PM extract, both as defined herein, in admixture with a physiologically—(i.e. pharmaceutically or dermatologically) acceptable carrier.

Thus, aspects of the present disclosure provide for a composition for topical treatment or prevention of skin aging including wrinkles, dehydration, loss of elasticity, oxidative stress, the composition comprising an anti-enzyme agent comprising the AR extract as defined herein, optionally in admixture with: one or more agent selected from the group of: hydrating agents, anti-microbial actives, anti-fungal actives, anti-inflammatory actives, exfoliating agents and mixtures thereof; and a physiologically-acceptable carrier. In one embodiment, the anti-enzyme agent comprises the AR or PM extract as defined herein effective for inhibiting elastase and/or collagenase and/or involucrine in a physiologically-acceptable carrier. By way of example, the composition may comprise between 0.05% and 20% of extract, and 80% to 99.95% (w/w) physiologically-acceptable carrier. Particularly the composition may comprise between 0.1% and 10%, more particularly between 0.1% and 5% (w/w) of extract.

Inactive Ingredients, Carriers and Formulations

The composition of the present invention may comprise, in addition to the active agent, one or more inactive ingredient selected from the group consisting of: carriers or excipients, viscosity or building agents, thickening agents, gelling agents and preservative agents.

The choice of a suitable physiologically-acceptable carrier will depend on the exact nature of the particular formulation desired, e.g. whether the present topical composition is to be formulated into a liquid solution, a suspension, an ointment, a film or a gel. The choice of a suitable physiologically-acceptable carrier will also depend on the route of administration. Preferably, the carrier is formulated to be suitable for topical administration.

Compositions suitable for topical application to the skin preferably take the form of an ointment, cream, salve, foam, lotion, paste, gel, spray, aerosol, or oil. Carriers that may be used include petroleum jelly, glycerine, lanoline, polyethylene glycols, alcohols (e.g., ethanol, isopropanol, etc.), transdermal enhancers, and combinations of two or more thereof.

In accordance with a particular embodiment, the inactive ingredient may be: glycerine, a polyacrylate, carbopol 940, 934,970,974, acacia, alginic acid, bentonite, carboxymethylcellulose, ethylcellulose, gelatin, hydroxyethylcellulose, hydroxypropyl cellulose, magnesium aluminum silicate, methylcellulose, poloxamers, polyvinyl alcohol, sodium alginate, tragacanth, and xanthan gum or mixtures thereof.

According to a particular embodiment, the extract is formulated in glycerin. More particularly, the extract is formulated at about 1% to about 10% by weight of dried extract in glycerin.

In still another embodiment, preservatives like paraben and triethanolamine may be added to increase the stability of the composition.

In the case of a topical formulation in a gel form, the carrier may be selected from the group consisting of: purified water; ammonium acryloyldimethyltaurate; VP colopolymer; aloe vera; edetate disodium; allantoin; methylchloroisothiazolinone; methylisothiazolinone; and mixtures thereof.

Alternatively, the present composition may be formulated as an anti-aging soap or detergent, for preventive or hygienic purposes. Particularly, in one embodiment, the anti-aging detergent comprises an extract of the present invention in combination with one or more additional cleaning composition components. The choice of additional components is within the skill of the artisan and includes conventional ingredients, including the exemplary non-limiting components set forth herein.

Alternatively, the present composition may be formulated in a microcrystalline form, in a liposomal preparation or as a wipe. The present composition may be formulated to be used as a cleanser or a toner. The present composition may be formulated to be used on the whole surface of a target skin area or for spot skin treatment. Formulations suitable for a desired route of administration are within the skill of one in the art.

Use and Method of Prevention

In accordance with an alternative aspect, the present invention provides the use of the extract as defined herein for inhibiting enzymes of skin epithelial cells. Particularly, there is provided the use of the extract as defined herein for the manufacture of composition for preventing aging in skin cells of a mammal.

In accordance with an alternative aspect of the invention, there is provided the use of the composition as defined herein for the prevention of skin aging in a mammal.

In accordance with a particular aspect, the present invention provides a method of inhibiting an enzyme comprising contacting said cell with a growth-inhibiting concentration of the extract as defined herein or the composition as defined herein.

More particularly, there is provided a method of prevention or treatment of skin aging in a mammal comprising administering an enzyme-inhibiting concentration of the composition as defined herein to said mammal. Most particularly, the mammal is a human subject.

In another aspect of the present disclosure, there is provided a method for the treatment of a skin disorder in a subject in need thereof, wherein the method comprises administering to the subject a therapeutically effective amount of a composition comprising an anti-enzymatic amount of the AR or PM extract as defined herein in admixture with a physiologically-acceptable carrier. In one embodiment, the administering is topical, whereby the treatment is applied to a skin area affected by wrinkles, dehydration, loss of elasticity and oxidative stress.

In another aspect of the present disclosure, there is provided a method of treating or preventing skin aging in a mammal, comprising contacting said skin with a skin-component synthesis-enhancing amount of a red maple bark solvent extract.

Compositions suitable for the present method are disclosed herein.

Anti-Wrinkle

In another aspect of the present disclosure, there is provided the composition as defined herein, wherein the extract is a red maple extract for use as anti-wrinkle on human skin.

In a further aspect, there is provided the red maple extract, for use as anti-wrinkle on human skin.

Elasticity

In accordance with a particular aspect, the present invention provides the composition as defined herein, for use in maintaining or increasing elasticity of human skin.

According to a particular embodiment, the invention provides the use as defined herein, for the manufacture of cosmetic composition for maintaining or increasing elasticity of human skin.

Firmness

In accordance with a particular aspect, the present invention provides the composition as defined herein, for use in maintaining of increasing firmness of human skin.

According to a particular embodiment, the present invention provides the use as defined herein, for the manufacture of cosmetic composition for maintaining of increasing firmness of human skin.

Enzymes Implicated in Aging

According to a particular aspect of the invention, enzymes associated with aging of the skin fibroblast cells are selected from the group consisting of: elastase and collagenase.

Synthesis of Protein Implicated in Skin Health

According to a particular aspect of the invention, skin-components associated with health are proteins from the skin fibroblast cells, and are selected from the group consisting of: elastin, collagen and involucrin.

Anti-Enzymatic Extract Concentration

According to a particular aspect, the present extract is present in the composition at a concentration of at least about 1 µg/ml to about 200 µg/ml, particularly between about 5 µg/ml to about 100 µg/ml.

According to a particular aspect, the extract of the invention inhibits elastase or collagenase by at least about 10%, 15% or 20%, particularly when tested in vitro under similar conditions as defined in the following examples.

According to a particular aspect, the extract of the invention promotes synthesis of elastin, collagenase or involucrin by at least about 10%, 15% or 20%, particularly when tested in vitro under similar conditions as defined in the following examples.

The following examples are put forth to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

EXAMPLES

This disclosure describes *Acer rubrum* harvesting, preparation of extract, and testing for anti-enzymatic activity.

Example 1—Aqueous Extraction

Conditioning of Raw Material
Reception of bark (visual inspection and removal of contaminants);
Drying bark pieces;
Gross grinding;
Fine comminuting to a granulometry of ≤800 µm;
Sieving, if necessary;
Stocking comminuted bark, away from light and humidity.
Extraction Under Reflux
Prepare the necessary weight of bark and put in a balloon large enough to contain solvent+30%;
Add distilled water according to a volume ratio raw material:water of about 1:16 (v/v);
Bring to 85° C.;
Time extraction for 1 hr;
Filter mixture on Büchner filter with Whatman #4;
Rinse the bark remaining on filter with a small volume of solvent.
Evaporation*
Dry solvent under pressure at a maximum temperature of 45° C.;
Recover powder and store in a glass container.
*Lyophilization, zeodratation or atomisation may also be used.

Example 2—Collagenase Inhibition

The evaluation of Red maple water extract effect on collagenase inhibition was carried out using the standard method EnzChek Gelatinase/Collagenase (Molecular Probes). Briefly, the extracts were diluted in a buffer solution (0.5M Tris-HCl, 1.5M NaCl, 50 mM $CaCl_2$ and 2 mM sodium azide; pH 7.6). 1,10-phenanthroline monohydrate (Sigma 320056) was used as positive control. Extracts (25, 50, 100 and 200 µg/mL) and positive control (18 µg/mL) were placed in a 96-well plate (80 uL). Collagen type 1 conjugated to fluorescein (20 µL) (MolecularProbes, D-12060) was added to all wells. Collagenase *clostridium* (Sigma, C0130) was also diluted in the reaction buffer to a final concentration of 0.1 U/mL and was added to the extract and positive control solutions (100 µL). The buffer solution was also added as a blank. The plate was then incubated at room temperature away from light for 2 hours. The fluorescence (λ excitation: 495 nm, λ emission: 515 nm) was measured using a VARIOSCAN fluorometer.

Collected data were transferred in SigmaStat™ 3.5 software. The intergroup comparisons were performed using the Wilcoxon signed rank test (P<0.05).

Collagenase inhibition by Red maple bark extract is presented in FIG. 1.

FIG. 1 shows the dose-dependent effect of Red maple bark extract on collagenase inhibition. At the level of 100 µg/mL, Red maple bark extract exhibits 62% inhibition of collagenase with a significant effect. Moreover, the inhibition effect of the extract was greater than the positive control 1,10-phenanthroline (18 µg/mL).

Under the experimental conditions of this study, collagenase enzyme activity is significantly reduced in the presence of Red maple bark extract, suggesting that this extract can act to limit collagen degradation.

Example 3—Stimulation of Collagen Type I in Skin Fibroblasts

The cytotoxicity of the extract was evaluated on skin fibroblasts (WS1, ATCC CRL-1502). Cells were seeded in 96-well plates at 5000 cells per well for the growth test, or to 10 000 cells per well to the test at confluence (cytotoxicity), in complete decomplemented culture medium. Cells were incubated overnight at 37° C. and 5% $CO_2$ to allow their adherence. The next day, the cells were treated or not with increasing concentrations of extract s ranging from 1.56 to 200 µg/mL. After 24 h, the cells were incubated with Resazurin (Sigma-Aldrich, R7017). The non-fluorescent Resazurin is reduced fluorescent resorufin by cellular metabolic activity (O'Brien et al. 2000). After an incubation period, the fluorescence is measured ($\lambda$ excitation: 530 nm, $\lambda$ emission: 590 nm). After the measurement of fluorescence, the supernatants are removed and the cells are frozen and lysed with sodium dodecyl sulfate (SDS) 0.01% and then quantifying the DNA by a test of Hoechst (Sigma-Aldrich, 861405).

The effect of the extract on collagen stimulation was evaluated using specific antibodies to type I Collagen. Once bound to collagen, the primary antibody is detected by a secondary antibody on which a fluorophore is grafted. Human skin fibroblasts (WS1, ATCC CRL-1502) were seeded in 96-well microplates in a full decomplemented culture medium and incubated overnight at 37° C. and 5% $CO_2$ to allow their adherence. Thereafter, the cells were incubated for 24 hours in the absence or presence of increasing concentrations of Red maple bark extract (12.5, 25, 50 and 100 µg/mL). The culture medium containing the extract was then removed and the cells were fixed with 95% ethanol for 10 minutes. The cells were washed three times with PBS and permeabilized with 0.5% Triton solution in PBS for 15 minutes. The cells were then incubated with the primary antibody (anti-collagen Calbiochem #234167) in solution 1/50 in 3% BSA overnight at 4° C. After three washes with PBS, the secondary antibody (Cy™ 2 AffiniPure Goat Anti-Mouse IgG, Jackson ImmunoResearch, Inc. Laboratories. #115-225-003) was added in solution 1:50 in 1×PBS for an hour. The secondary antibody was then removed with three washes with PBS. The fluorescence emitted by the secondary antibody was then measured and pictures were taken with a fluorescence microscope Cytation3.

Figure 2A:
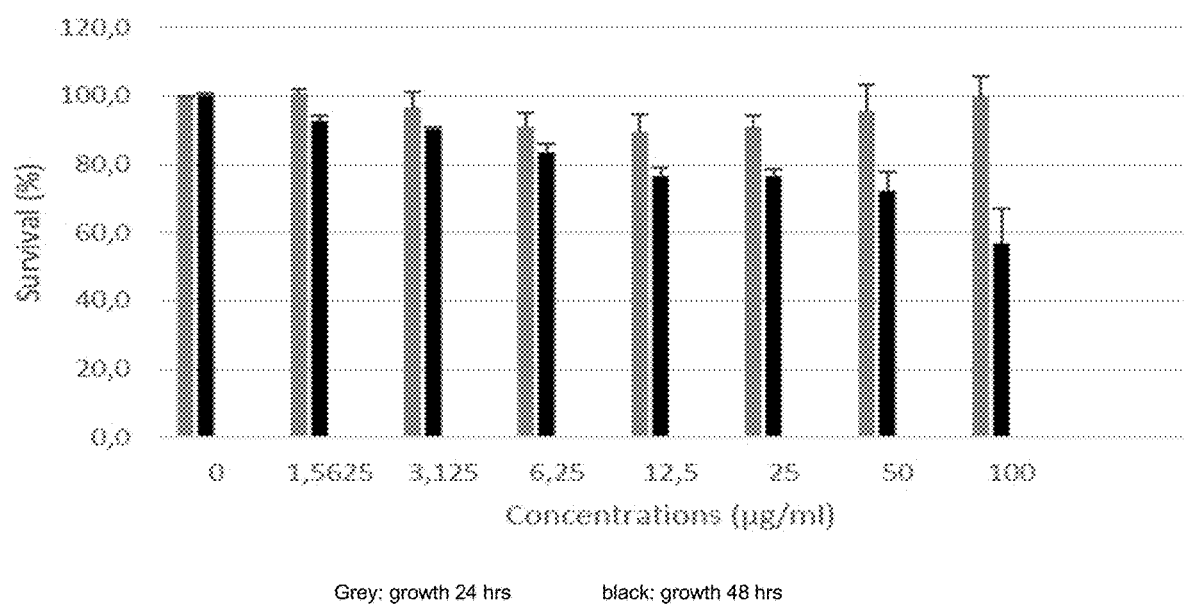
FIG. 2A. Effect of Red maple bark extract on cell survival after 24H and 48H-Resazurin.
Figure 2B:
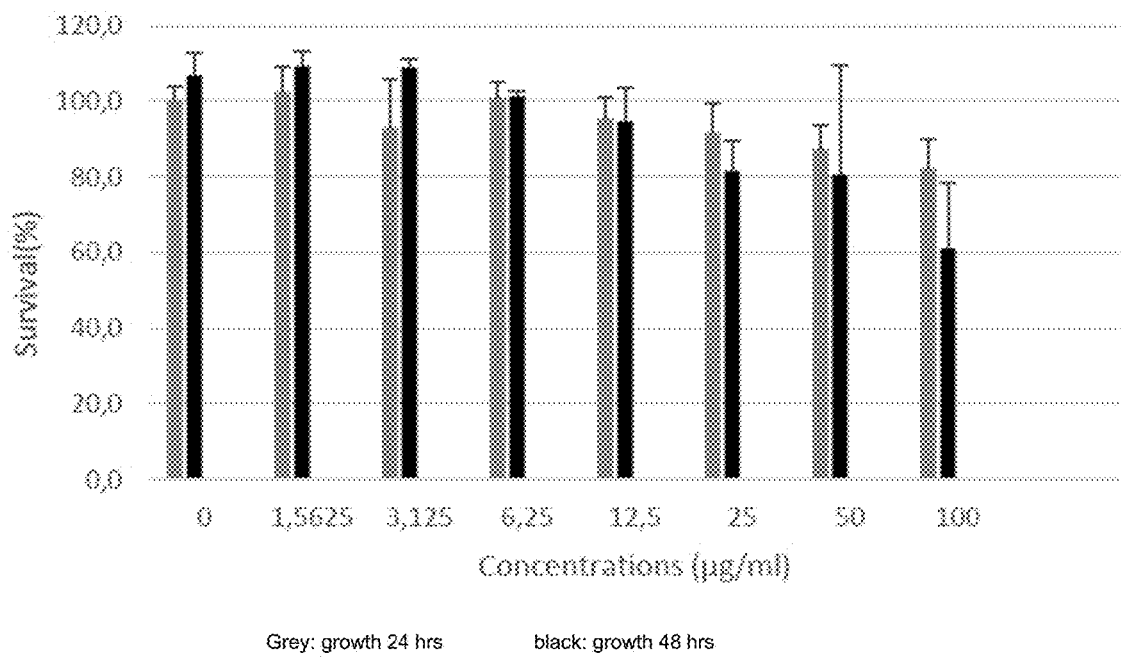
FIG. 2B. Effect of Red maple bark extract on cell survival after 24H and 48H-Hoechst.

FIG. 2 shows the survival percentage of human skin fibroblasts in function of the concentration of Red maple bark extract (1.56 to 200 µg/mL). Two probes were used to evaluate the survival: Resazurin (FIG. 2A) and Hoechst (FIG. 2B). The effect of extracts on survival was assessed in cell growth as well as confluent cells after 24. The results (FIG. 2A) showed that 100 and 200 µg/mL of Red maple bark extract significantly affect the metabolism of the cells in growth after 48 hours with a decrease, respectively, 43% and 74%. At 200 µg/mL of the extract, cell survival and growth of confluent cells (Hoescht test, FIG. 2B) are significantly affected with respective survival rates of 59% and 72% after 24 hours and 25% and 56% after 48 hours. Therefore, the maximum concentration of Red maple bark extract that was used for the subsequent cellular studies was also set at 100 µg/mL.

The results presented in FIG. 3 are expressed as percent increase in fluorescence of the treated cells compared to untreated cells. TGF-$\beta$ (10 ng/mL) was used as positive control with a significant average increase of 56%. FIG. 4 shows pictures taken with the fluorescence microscope Cytation3 which illustrate collagen synthesis in presence or not of Red maple bark extract in fibroblasts.

FIG. 3 shows a dose-dependent effect of Red maple bark extract on collagen synthesis in human fibroblast with an increase of 100% of collagen production at the concentration of 100 µg/mL.

FIG. 4 demonstrates a high efficacy on collagen synthesis of Red maple bark extract at 100 µg/mL after 24 h incubation in skin fibroblasts. Clear collagen clusters can be observed on the picture of FIG. 4B (in presence of Red maple bark extract) and be compared to the positive control (picture of FIG. 4C).

The results obtained demonstrate that Red maple bark extract stimulates significantly collagen production in skin fibroblasts.

Example 4—Stimulation of Elastin by Red Maple Extract

The cytotoxicity of the extract was evaluated on human skin fibroblasts (WS1, ATCC CRL-1502).

Cells were seeded in 96-well plates at 5000 cells per well for the growth test, or to 10 000 cells per well to the test at confluence (cytotoxicity), in a decomplemented complete culture medium. Cells were incubated overnight at 37° C. and 5% $CO_2$ to allow their adherence. The next day, the cells were treated or not with increasing concentrations of extracts ranging from 12.5 to 100 µg/mL. After 24 h or 48 h, the cells were incubated with Resazurin (Sigma-Aldrich, R7017). The non-fluorescent Resazurin is reduced fluorescent resorufin by cellular metabolic activity (O'Brien et al. 2000). After an incubation period, the fluorescence is measured ($\lambda$ excitation: 530 nm, $\lambda$ emission: 590 nm). After the measurement of fluorescence, the supernatants are removed and the cells are frozen and lysed with sodium dodecyl sulfate (SDS) 0.01% and then quantifying the DNA by a test of Hoechst (Sigma-Aldrich, 861405).

The effect of the extract on stimulating elastin production was assessed using specific antibodies elastin (anti-elastin, #21610, Abcam). Once bound to elastin, the primary antibody is detected by a secondary antibody to which is grafted a fluorophore. Human skin fibroblasts (WS1, ATCC CRL-1502) were seeded in 96-well microplates in the middle of full decomplemented culture and incubated overnight at 37° C. and 5% CO2 to allow their adherence. Thereafter, the cells were incubated for 24 hours in the absence or presence of increasing concentrations of Red maple bark extract, native extract solutions (12.5, 25, 50 and 100 µg/mL). The culture medium containing the extract solutions was then removed and the cells were fixed with 95% ethanol for 10 minutes. The cells were washed three times with PBS and permeabilized with 0.5% Triton solution in PBS for 15 minutes. The cells were then incubated with the primary antibody solution 1/50 in 3% BSA overnight at 4° C. After three washes with PBS, the secondary antibody (Cy™ 2 AffiniPure Goat Anti-Mouse IgG, Jackson ImmunoResearch, Inc. Laboratories. #115-225-003) was added in solution 1:50 in 1×PBS for an hour. The secondary antibody was then removed with three washes with PBS. The fluorescence emitted by the secondary antibody was then measured and pictures were taken with a fluorescence microscope Cytation3.

Collected data were transferred in SigmaStat 3.5 software. The intergroup comparisons were performed using the Wilcoxon signed rank test (P<0.05).

Figure 5A:
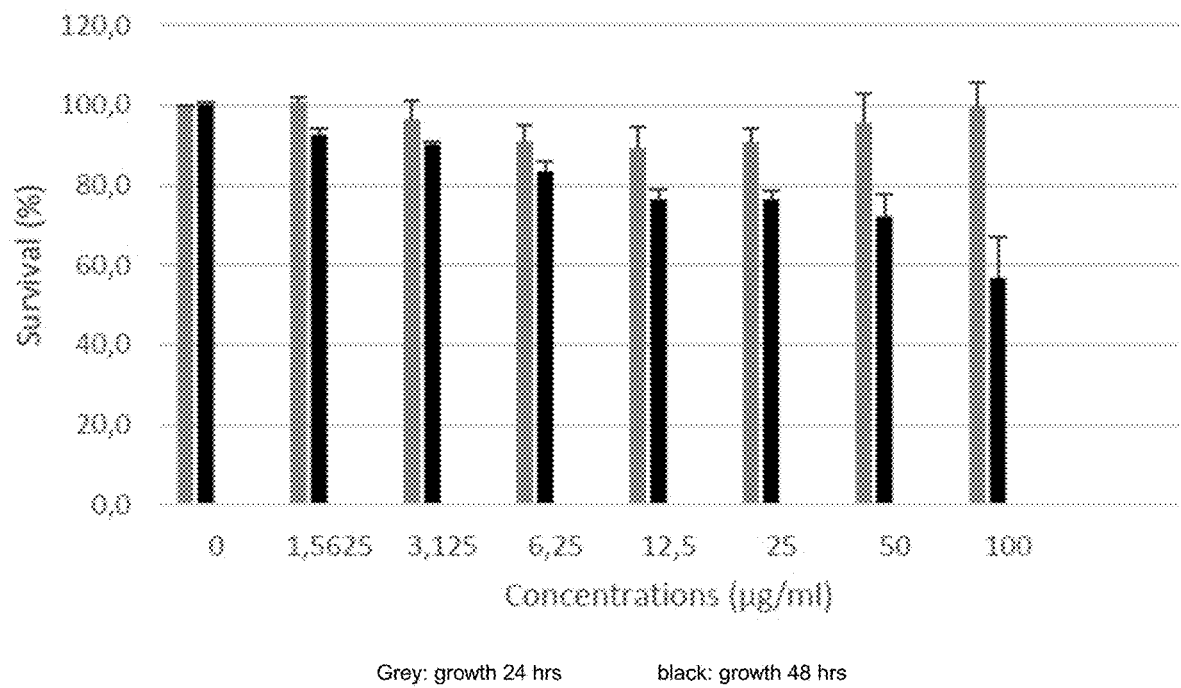
FIG. 5A. Effect of Red maple bark extract on cell survival after 24H and 48H-Resazurin.
Figure 5B:
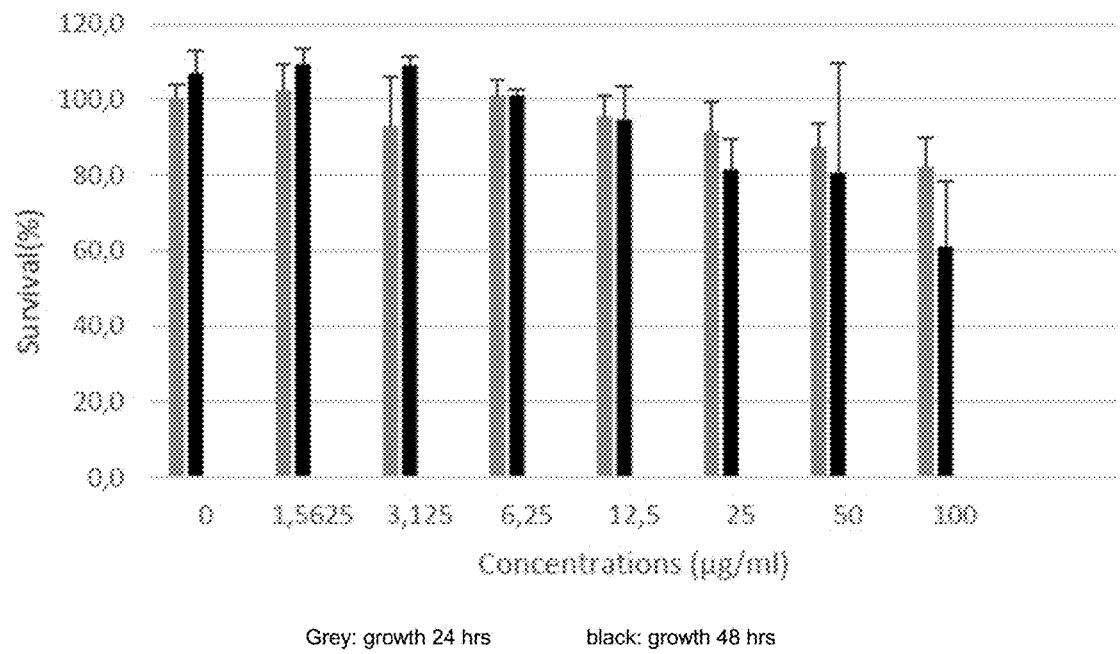
FIG. 5B. Effect of Red maple bark extract on cell survival after 24H and 48H-Hoechst.

FIG. 5 shows the survival percentage of human skin fibroblasts in function of the concentration of Red maple bark extract (1.56 to 200 µg/mL). Two probes were used to evaluate the survival: Resazurin (FIG. 5A) and Hoechst (FIG. 5B). The effect of extracts on survival was assessed in cell growth as well as confluent cells after 24. The results (FIG. 5A) showed that 100 and 200 µg/mL of Red maple bark extract significantly affect the metabolism of the cells in growth after 48 hours with a decrease, respectively, 43% and 74%. At 200 µg/mL of the extract, cell survival and growth of confluent cells (Hoescht test, FIG. 5B) are significantly affected with respective survival rates of 59% and 72% after 24 hours and 25% and 56% after 48 hours. Therefore, the maximum concentration of Red maple bark extract that was used for the subsequent cellular studies was also set at 100 µg/mL.

Figure 6:
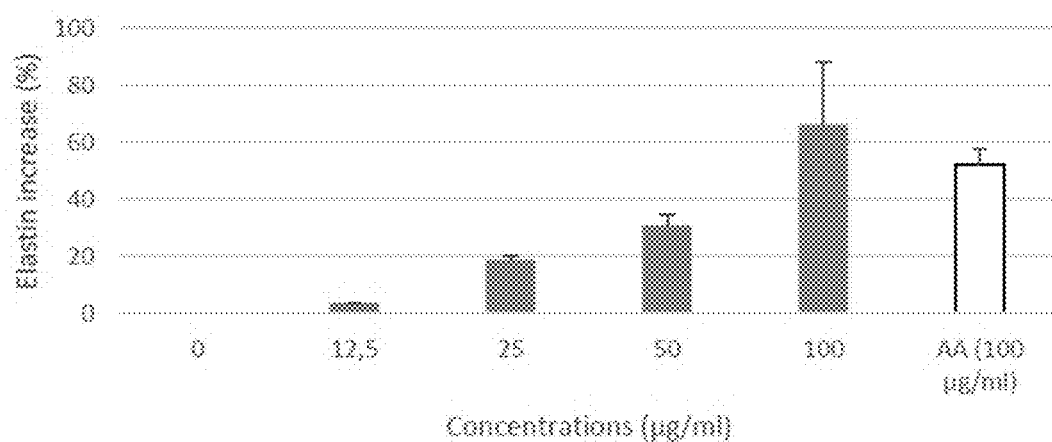
FIG. 6. Effect of Red maple bark extract on elastin stimulation. Skin fibroblasts were incubated with and without the presence of increasing concentrations of the extract. The cells were then fixed and incubated with an antibody against elastin. The results are expressed as a percentage of the elastin increase after 48 h compared to untreated cells. Ascorbic acid (AA) was used as a positive control. The data is significantly different from untreated cells; P<0.05; Wilcoxon signed Rank Test. (SigmaStat™ 3.5)
Figure 7:
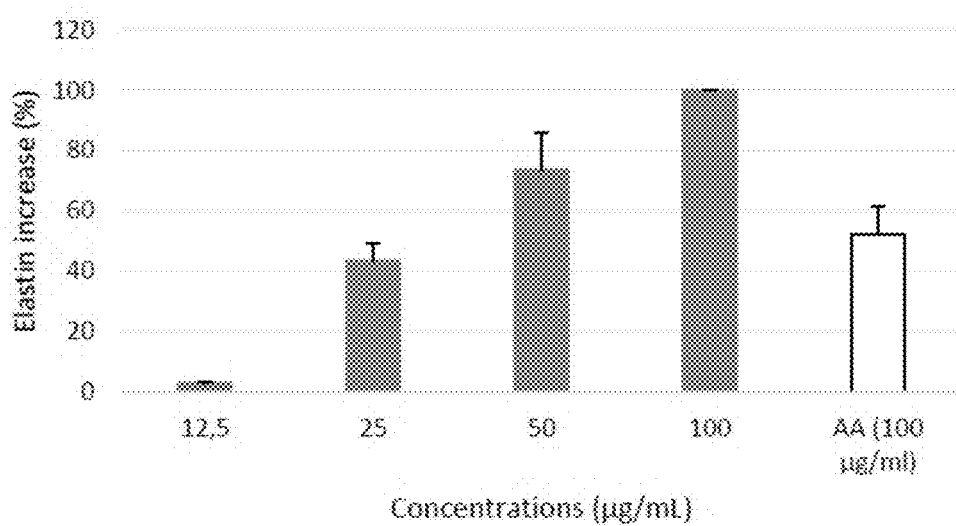
FIG. 7. Red maple bark extract's effect on elastin stimulation. Skin fibroblasts were incubated with and without the presence of increasing concentrations of the extract. The cells were then fixed and incubated with an antibody against elastin. The results are expressed as a percentage of the elastin increase after 48 h compared to untreated cells. Ascorbic acid (AA) was used as a positive control. The data is significantly different from untreated cells; P<0.05; Wilcoxon signed Rank Test. (SigmaStat™ 3.5)

Stimulation of elastin production by Red maple bark extract after 24 h and 48 h are presented in FIGS. 6 and 7.

FIGS. 6 and 7 show the dose-dependent effect of Red maple bark extract on elastin stimulation. At the level of 100 µg/mL, Red maple bark extract native extract allow to increase the elastin level of 66% after 24 h and 100% after 48 h.

The increase in elastin induced by 100 µg/mL of Red maple bark extract was visualized by fluorescent microscopy. FIG. 8 shows a high increase in elastin that can be observed by fluorescent zones and this can be compared to the positive control effect.

Under the experimental conditions of this study, the production of elastin is increased in the presence of Red maple bark extract, suggesting that this extract has an effect on dermal regeneration.

Example 5—Stimulation of Involucrin in Skin Keratinocytes from Red Maple Bark Extract The effect of Red maple bark extract on the involucrin stimulation was performed using specific antibodies to involucrin (anti-involucrin, ab28057, Abcam). Once attached to involucrin, the primary antibody is detected by a secondary antibody to which is grafted a fluorophore. Keratinocytes from human skin were seeded in 96-well microplates in complete decomplemented culture medium and incubated overnight at 37° C. and 5% $CO_2$ to allow their adherence. Thereafter, the cells were incubated for 24 hours in the absence or presence of increasing concentrations of Red maple bark extract from 12.5 to 100 µg/mL. The culture medium containing the extract was then removed and the cells were fixed with 95% ethanol for 10 minutes. The cells were washed three times with PBS and permeabilized with 0.5% Triton solution in PBS for 15 minutes. The cells were then incubated with the primary antibody solution 1/50 in 3% BSA overnight at 4° C. After three washes with PBS, the secondary antibody (Cy™ 2 AffiniPure Goat Anti-Mouse IgG, Jackson ImmunoResearch, Inc. Laboratories. #115-225-003) was added in solution 1:50 in PBS for an hour. The secondary antibody was then removed with three washes with PBS. The fluorescence emitted by the secondary antibody was then measured and pictures were taken with a fluorescence microscope Cytation3.

Collected data were transferred in SigmaStat 3.5 software. The intergroup comparisons were performed using the Wilcoxon signed rank test test ($P<0.05$).

Stimulation of involucrin production by Red maple bark extract is presented in FIG. 9.

The results presented in FIG. 9 show that Red maple bark extract significantly stimulates the synthesis of involucrin with a production increase of 28% at 100 µg/mL.

Under the experimental conditions of this study, the production of involucrin is stimulated in the presence of Red maple bark extract, suggesting that this extract has an action on cellular differentiation.

Conclusion

We demonstrated that crude bark extracts, without any procedure of fractionation and purification, exhibit anti-aging effectiveness which indicates that this extract can find applications as cosmetic products, not only to prevent damage provoked by oxidative stress in the human organism, but also as a specific inhibitors of skin degradation enzymes and as a stimulator of healthy skin components.

Finally, we anticipate a real potential for the application of red maple bark extract following the integration of the extraction units into the existing forest industry mills, which will be thus transformed into biorefineries of the future.

Example 6—Collagenase Inhibition by Black Spruce Extract

The evaluation of Black spruce water extract (as made according to the protocol of Example 1) effect on collagenase inhibition was carried out using the standard method EnzChek Gelatinase/Collagenase (Molecular Probes). Briefly, the extracts were diluted in a buffer solution (0.5M Tris-HCl, 1.5M NaCl, 50 mM $CaCl_2$ and 2 mM sodium azide; pH 7.6). 1,10-phenanthroline monohydrate (Sigma 320056) was used as positive control. Extracts (25, 50, 100 and 200 µg/mL) and positive control (18 µg/mL) were placed in a 96-well plate (80 µL). Collagen type 1 conjugated to fluorescein (20 µL) (MolecularProbes, D-12060) was added to all wells. Collagenase *clostridium* (Sigma, C0130) was also diluted in the reaction buffer to a final concentration of 0.1 U/mL and was added to the extract and positive control solutions (100 µL). The buffer solution was also added as a blank. The plate was then incubated at room temperature away from light for 2 hours. The fluorescence ($\lambda$ excitation: 495 nm, $\lambda$ emission: 515 nm) was measured using a VARIOSCAN fluorometer.

Collected data were transferred in SigmaStat™ 3.5 software. The intergroup comparisons were performed using the Wilcoxon signed rank test ($P<0.05$).

Figure 10:
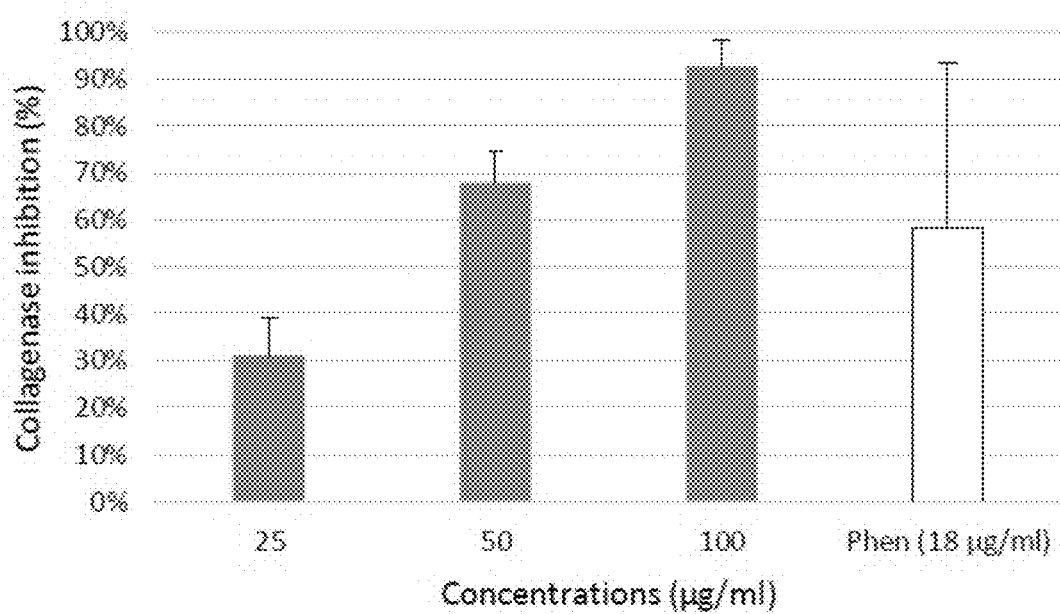
FIG. 10. Collagenase inhibition by Black spruce bark extract. The collagenase was incubated both with and without the presence of increasing concentrations of the extract. The results are expressed as a percentage of the collagenase activity inhibition compared with the enzyme only. The 1,10-phenanthroline was used as a positive control. The data is significantly different from enzyme+substrate only; P<0.05; Wilcoxon signed Rank Test (SigmaStat™ 3.5).

Collagenase inhibition by Black spruce bark extract is presented in FIG. 10.

FIG. 10 shows the dose-dependent effect of Black spruce bark extract on collagenase inhibition. At the level of 100 µg/mL, Black spruce bark extract exhibits 91% inhibition of collagenase with a significant effect. Moreover, the inhibition effect of the extract was greater than the positive control 1,10-phenanthroline (18 µg/mL).

Under the experimental conditions of this study, collagenase enzyme activity is significantly reduced in the presence of Black spruce bark extract, suggesting that this extract can act to limit collagen degradation.

Example 7—Stimulation of Collagen Type I Synthesis in Skin Fibroblasts by Black Spruce Extract Preliminary Cytotoxicity Test The cytotoxicity of the extract was evaluated on skin fibroblasts (WS1, ATCC CRL-1502). Cells were seeded in 96-well plates at 5000 cells per well for the growth test, or to 10 000 cells per well to the test at confluence (cytotoxicity), in complete decomplemented culture medium. Cells were incubated overnight at 37° C. and 5% $CO_2$ to allow adherence. The next day, the cells were treated or not with increasing concentrations of extracts ranging from 1.56 to 200 µg/mL. After 24 h, the cells were incubated with Resazurin (Sigma-Aldrich, R7017). The non-fluorescent Resazurin is reduced fluorescent resorufin by cellular metabolic activity (O'Brien et al. 2000). After an incubation period, the fluorescence is measured ($\lambda$ excitation: 530 nm, $\lambda$ emission: 590 nm). After the measurement of fluorescence, the supernatants are removed and the cells are frozen and lysed with sodium dodecyl sulfate (SDS) 0.01% and then DNA is quantified by the Hoescht test (Sigma-Aldrich, 861405).

Figure 11A:
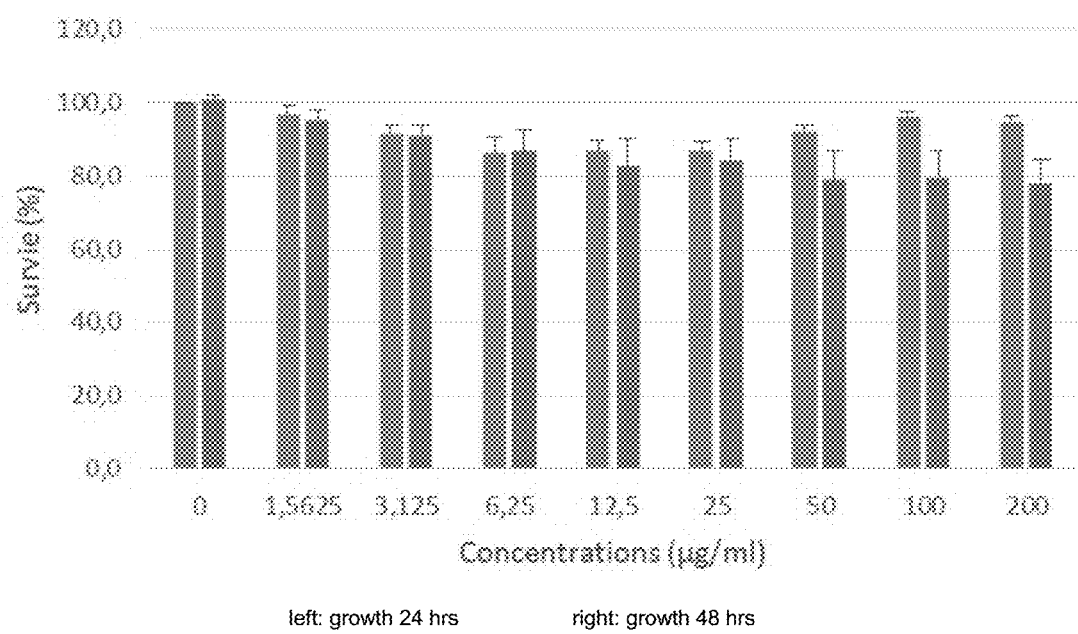
FIG. 11A. Effect of Black spruce bark extract on cell survival after 24H and 48H-Resazurin.
Figure 11B:
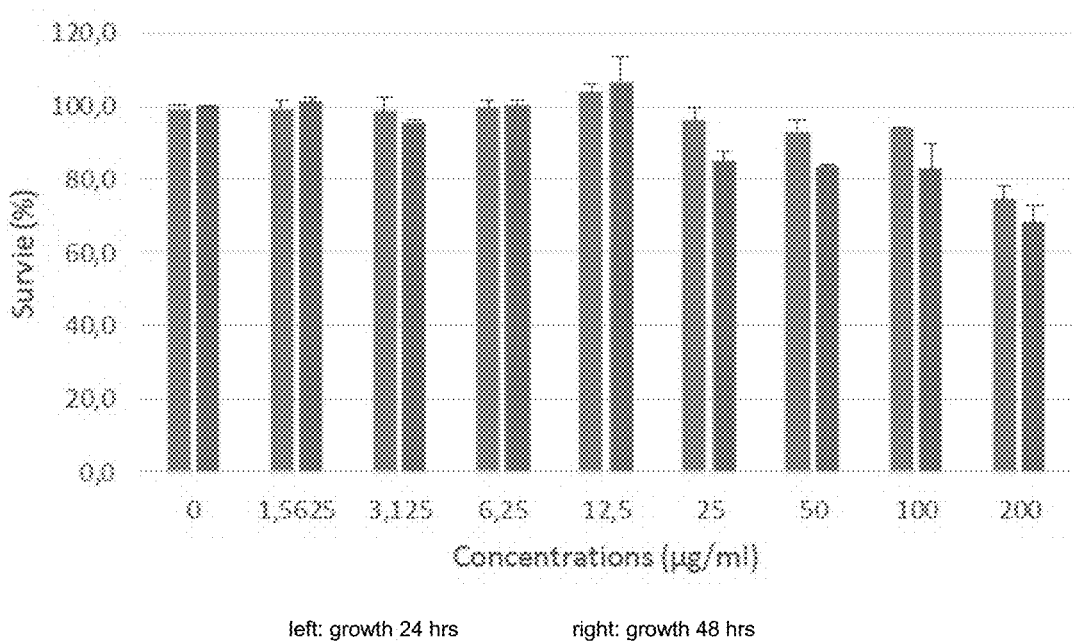
FIG. 11B. Effect of Black spruce bark extract on cell survival after 24H and 48H-Hoechst.

FIG. 11 shows the survival percentage of human skin fibroblasts in function of the concentration of Black spruce bark extract (1.56 to 200 μg/mL). Two probes were used to evaluate the survival: Resazurin (FIG. 11A) and Hoecht (FIG. 11B). The effect of extract on survival was assessed in cell growth as well as confluent cells after 24. The results (FIG. 11A) showed that 200 μg/mL of Black spruce bark extract significantly affect the metabolism of the cells in growth after 48 hours with a decrease, of 22% (significant). At 200 μg/mL of the extract, cell survival and growth of confluent cells (Hoescht test, FIG. 11B) are not significantly affected with decrease of 28% after 48 hours. Therefore, the maximum concentration of Black spruce bark extract that was used for the subsequent cellular studies was set at 100 μg/mL.

Cytotoxicity on keratinocytes was evaluated by imagery and no toxicity was observed in the range of tested concentrations.

Collagen Synthesis

The effect of the extract on collagen stimulation was evaluated using specific antibodies to type I Collagen. Once bound to collagen, the primary antibody is detected by a secondary antibody on which a fluorophore is grafted. Human skin fibroblasts (WS1, ATCC CRL-1502) were seeded in 96-well microplates in a full decomplemented culture medium and incubated overnight at 37° C. and 5% $CO_2$ to allow their adherence. Thereafter, the cells were incubated for 24 hours in the absence or presence of increasing concentrations of Black spruce bark extract (12.5, 25, 50 and 100 μg/mL). The culture medium containing the extract was then removed and the cells were fixed with 95% ethanol for 10 minutes. The cells were washed three times with PBS and permeabilized with 0.5% Triton solution in PBS for 15 minutes. The cells were then incubated with the primary antibody (anti-collagen Calbiochem #234167) in solution 1/50 in 3% BSA overnight at 4° C. After three washes with PBS, the secondary antibody (Cy™ 2 AffiniPure Goat Anti-Mouse IgG, Jackson ImmunoResearch, Inc. Laboratories. #115-225-003) was added in solution 1:50 in 1×PBS for an hour. The secondary antibody was then removed with three washes with PBS. The fluorescence emitted by the secondary antibody was then measured and pictures were taken with a fluorescence microscope Cytation3.

The results presented in FIG. 12 are expressed as percent increase in fluorescence of the treated cells compared to untreated cells. TGF-β (10 ng/mL) was used as positive control with a significant average increase of 56%. FIG. 13 shows pictures taken with the fluorescence microscope Cytation3 which illustrate collagen synthesis in presence or not of Black spruce bark extract in fibroblasts.

FIG. 12 shows a dose-dependent effect of Black spruce bark extract on collagen synthesis in human fibroblast with an increase of 100% of collagen production at the concentration of 100 μg/mL.

FIG. 13 demonstrates a high efficacy on collagen synthesis of Black spruce bark extract at 100 μg/mL after 24 h incubation in skin fibroblasts. Clear collagen clusters can be observed on the picture of FIG. 13B (in presence of Black spruce bark extract) and be compared to the positive control (picture of FIG. 13C).

The results obtained demonstrate that Black spruce bark extract stimulates significantly collagen production in skin fibroblasts.

Example 8—Stimulation of Elastin Production by Black Spruce Extract

Preliminary Cytotoxicity Test

The cytotoxicity of the Black spruce extract was evaluated on human skin fibroblasts (WS1, ATCC CRL-1502). Cells were seeded in 96-well plates at 5000 cells per well for the growth test, or to 10 000 cells per well to the test at confluence (cytotoxicity), in a decomplemented complete culture medium. Cells were incubated overnight at 37° C. and 5% $CO_2$ to allow their adherence. The next day, the cells were treated or not with increasing concentrations of extracts ranging from 12.5 to 100 μg/mL. After 24 h or 48 h, the cells were incubated with Resazurin (Sigma-Aldrich, R7017). The non-fluorescent Resazurin is reduced fluorescent resorufin by cellular metabolic activity (O'Brien et al. 2000). After an incubation period, the fluorescence is measured (λ excitation: 530 nm, λ emission: 590 nm). After the measurement of fluorescence, the supernatants are removed and the cells are frozen and lysed with sodium dodecyl sulfate (SDS) 0.01% and then the DNA is quantified by the Hoechst test (Sigma-Aldrich, 861405).

Figure 14A:
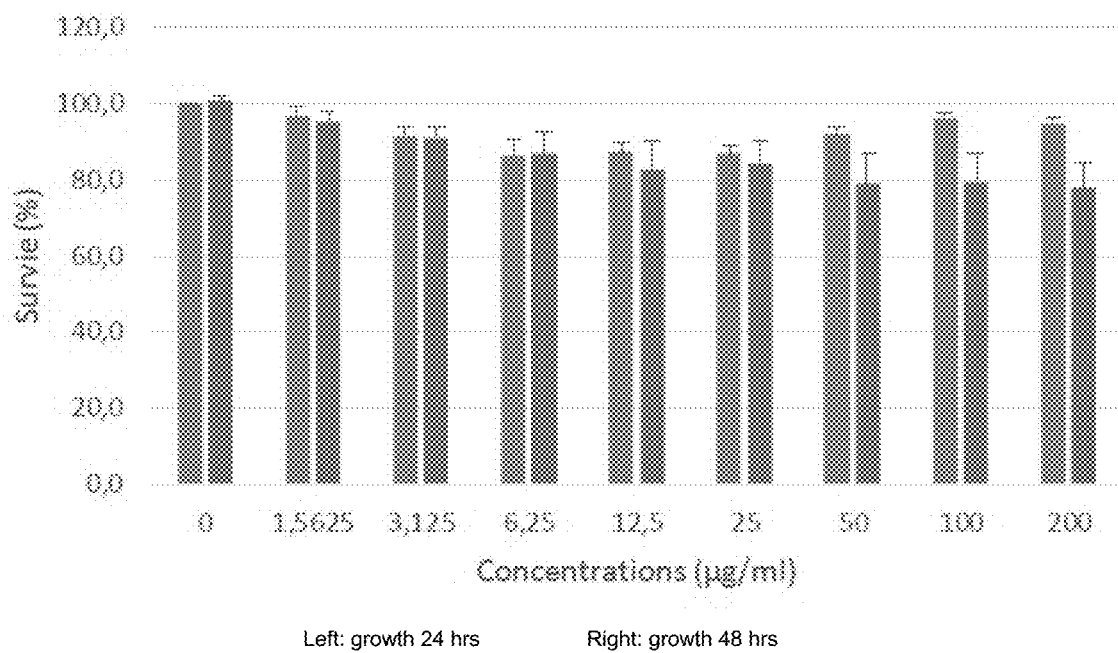
FIG. 14A. Effect of Black spruce bark extract on cell survival after 24H and 48H-Resazurin.
Figure 14B:
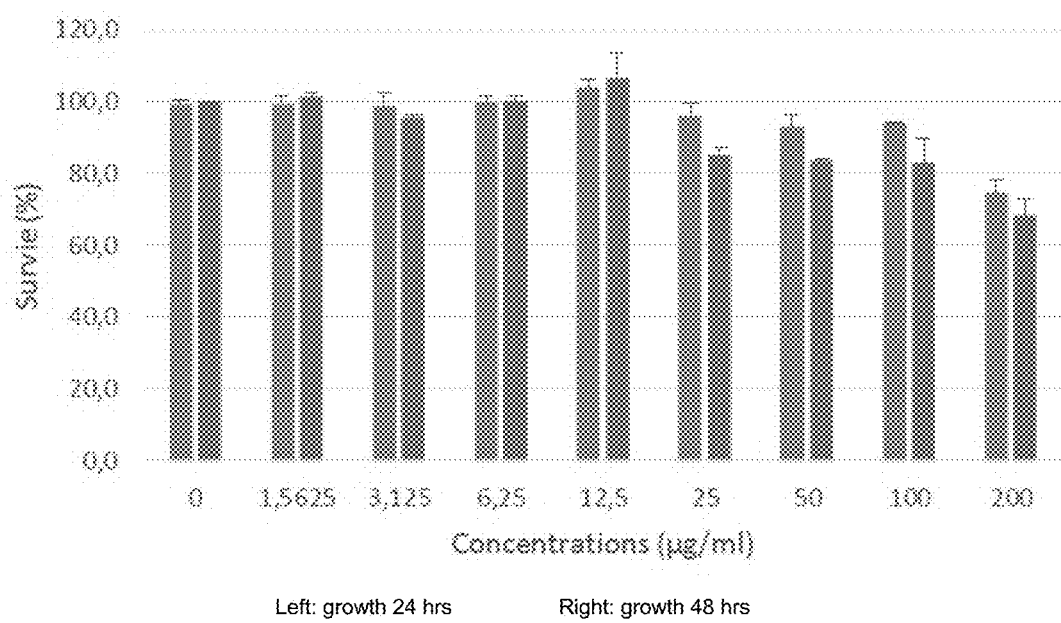
FIG. 14B. Effect of Black spruce bark extract on cell survival after 24H and 48H-Hoechst FIG. 15. Effect of Black spruce bark extract on elastin stimulation. Skin fibroblasts were incubated with and without the presence of increasing concentrations of the extract. The cells were then fixed and incubated with an antibody against elastin. The results are expressed as a percentage of the elastin increase after 24 h compared to untreated cells. Ascorbic acid (AA) was used as a positive control. The data is significantly different from untreated cells; P<0.05; Wilcoxon signed Rank Test. (SigmaStat™ 3.5)

FIG. 14 shows the survival percentage of human skin fibroblasts in function of the concentration of Black spruce bark extract (1.56 to 200 μg/mL). Two probes were used to evaluate the survival: Resazurin (FIG. 14A) and Hoechst (FIG. 14B). The effect of extracts on survival was assessed in cell growth as well as confluent cells after 24 h. The results (FIG. 14A) showed that 200 μg/mL of Black spruce bark extract significantly affect the metabolism of the cells in growth after 48 hours with a decrease of 22% (significant) . At 200 μg/mL of the extract, cell survival and growth of confluent cells (Hoescht test, FIG. 14B) are not significantly affected with a decrease of 28% after 48 hours. Therefore, the maximum concentration of Black spruce bark extract that was used for the subsequent cellular studies was also set at 100 μg/mL.

Cytotoxicity on keratinocytes was evaluated by imagery and no toxicity was observed in the range of tested concentrations.

Elastin Stimulation Assay

The effect of the extracts on stimulating elastin production was assessed using specific antibodies elastin (anti-elastin, #21610, Abcam). Once bound to elastin, the primary antibody is detected by a secondary antibody to which is grafted a fluorophore. Human skin fibroblasts (WS1, ATCC CRL-1502) were seeded in 96-well microplates in the middle of full decomplemented culture and incubated overnight at 37° C. and 5% $CO_2$ to allow for adherence. Thereafter, the cells were incubated for 24 hours in the absence or presence of increasing concentrations of Black spruce bark extract, native extract solutions (12.5, 25, 50 and 100 μg/mL). The culture medium containing the extract solution was then removed and the cells were fixed with 95% ethanol for 10 minutes. The cells were washed three times with PBS and permeabilized with 0.5% Triton solution in PBS for 15 minutes. The cells were then incubated with the primary antibody solution 1/50 in 3% BSA overnight at 4° C. After three washes with PBS, the secondary antibody (Cy™ 2 AffiniPure Goat Anti-Mouse IgG, Jackson ImmunoResearch, Inc. Laboratories. #115-225-003) was added in solution 1:50 in 1×PBS for an hour. The secondary antibody was then removed with three washes with PBS. The fluorescence emitted by the secondary antibody was then measured and pictures were taken with a fluorescence microscope Cytation3.

Collected data were transferred in SigmaStat 3.5 software. The intergroup comparisons were performed using the Wilcoxon signed rank test (P<0.05).

Stimulation of elastin production by Black spruce bark extract after 24 h and 48 h is presented in FIG. 15 that shows the dose-dependent effect of Black spruce bark extract on elastin stimulation. At the level of 100 μg/mL, Black spruce bark extract native extract induces an increase of 65% in the elastin level after 24 h.

The increase in elastin induced by 100 μg/mL of Black spruce bark extract was visualized by fluorescent microscopy. FIG. 16 shows a high increase in elastin that can be observed by fluorescent zones and this can be compared to the positive control effect.

Under the experimental conditions of this study, the production of elastin is increased in the presence of Black spruce bark extract, suggesting that this extract has an effect on dermal regeneration.

Example 9—Protection to UV by Black Spruce Bark Extract

In the present study, the UV protection activity of Black spruce bark extract was evaluated in vitro via the extract's absorbency measure.

Preliminary Cytotoxicity Test

The UV protector effect of Black spruce bark extract was evaluated in vitro by spectrophotometer. The extract was dissolved in ethanol at 20 μg/ml (Les Alcools du Commerce, 019211). Likewise, the homosalate standard was dissolved in the same solvent and at the same concentration. The fluorescence is measured from 400 nm to 200 nm, with the formula $SPF=CF \times \Sigma_{290}^{320} EE \times I \times Abs$, where EE, I and CF are known constants. The SPF was calculated according to Gupta, 2013.

Data Processing

The data was transferred in Microsoft Excel® software. The intergroup comparisons were performed using the Wilcoxon signed rank test (P<0.05). UV protector effect by Black spruce bark extract is presented in Table 2.

TABLE 2

| Information about the tested product | |
|---|---|
| Product | SPF |
| EN1502/F8BFX-01 | 2.1 ± 0.2 |
| EN1502/F2BFX-02 | 1.9 ± 0.1 |
| EN1502/F7BFX-01 | 2.0 ± 0.2 |
| Homosalate | 3.9 ± 0.2 |

Table 2 shows the effect of Black spruce bark extract on UV protection. At a level of 20 μg/mL, Black spruce bark extract has an average SPF of 2 which is an order of magnitude that is comparable to that of positive control homosalate.

Under the experimental conditions of this study, the FPS of Black spruce bark extract is 2, suggesting an UV protection effect.

Example 10—Protection to UV by Black Spruce Bark Extract

In the present study, the efficacy evaluation of the barrier effect of Black spruce bark extract (0.5% in base cream) was evaluated in vivo by the Trans-epidermal Water Loss (TWEL) measure.

Environmental Conditions

The study has been carried out in standard environmental conditions, for each measurement time point, by monitoring and maintaining constant the environmental temperature and humidity.

Treated Areas

The products under examination, base cream and cream containing Black spruce extract were applied by a technician. The technician applied the products on the inner forearm of the volunteer. The assignment of the inner forearm (left and right) where made randomly.

Evaluated Skin Areas

The measurements of TEWL was carried out in duplicate for each subject for each experimental time at the level of the treated area. The two skin points analysed at different times were as much as possible superimposable for each time analysis.

Mode of Application

The products were applied in no occlusive epicutaneous application, massaging until absorbed. The amount of product applied in each application was approximately 2 mg/cm², according to the Colipa Guidelines. The day of the measurements the volunteers were asked to keep the area under examination free of all cosmetic products.

Study Duration

The treatment has been carried out for 1 day for each volunteer. The products under study were applied once at the beginning of the study.

Preparation of the Volunteers

Before each measurement with the Tewameter®, each volunteer was allowed to relax for approximately 10 minutes in an air-conditioned room to avoid anomalous sampling due to excessive sweating or stress.

Measurement of the Trans-Epidermal Water Loss (TEWL)

The measurement of trans-epidermal water loss (TEWL) through Tewameter® TM300 (Courage-Khazaka GmbH, Germany) is an internationally accepted standard method of measurement. The measurement of the water evaporation is based on the diffusion principle in an open chamber. The open chamber measurement method is the only method to assess the TEWL continuously, which is necessary for most applications without influencing the skin surface. The tool is an evaporimeter which measures the water vapor released from a surface, through Fick's law:

$$d_m/d_t = <<-D \times A \times dp/dx, \text{ where:}$$

A=surface in m²
M=water transported (in g)
t=time (hours)
D=diffusion constant (0.0877 g/m(h(mmHg))
p=vapour pressure of the atmosphere (mm Hg)
x=distance from skin surface to point of measurement (m).

The diffusion law $d_m/d_t$ shows the amount of water transported by cm² in a unit time (hours); TEWL values are measured in g/h/m². The degree of water vapor diffusion is directly dependent, on the thickness of stratum corneum.

Subjects' Selection

The study was performed on 20 volunteers, aged from 18 to 65, selected with hairless arms. They were identified from the database of volunteers of the Abich Test Center, and who were evaluated as appropriate for participation in the study and not suffering from diseases to the skin areas to treat. Only volunteers in good health conditions were included in the study. All volunteers signed a consent allowing to treat personal data according to Quebec Law.

Instrumentation and Materials

The following instrumentation and materials were used: Multiprobe Adapter Systems MPA®, equipped with eight probes managed by a single software, among which CM285 the Environmental Thermo-hygrometer "Traceable" (Fisher Scientific).

Measurements of TEWL

The TEWL was evaluated at time T0, before product's application, during the application at T1 (10 minutes), T2 (30 minutes), T3 (1 hour), T4 (4 hours) and T5 (8 hours) of product application. The TEWL measurements were carried out in duplicate on the treated area of each volunteer, respectively and the means of the measurements were extrapolated for each experimental time.

Statistical Analysis

The distribution of the values obtained during the measurements at the experimental times for the zone treated with the product were compared with an inter-group analysis and intra-group analysis using Student's t test ($P<0.05$).

Figure 17:
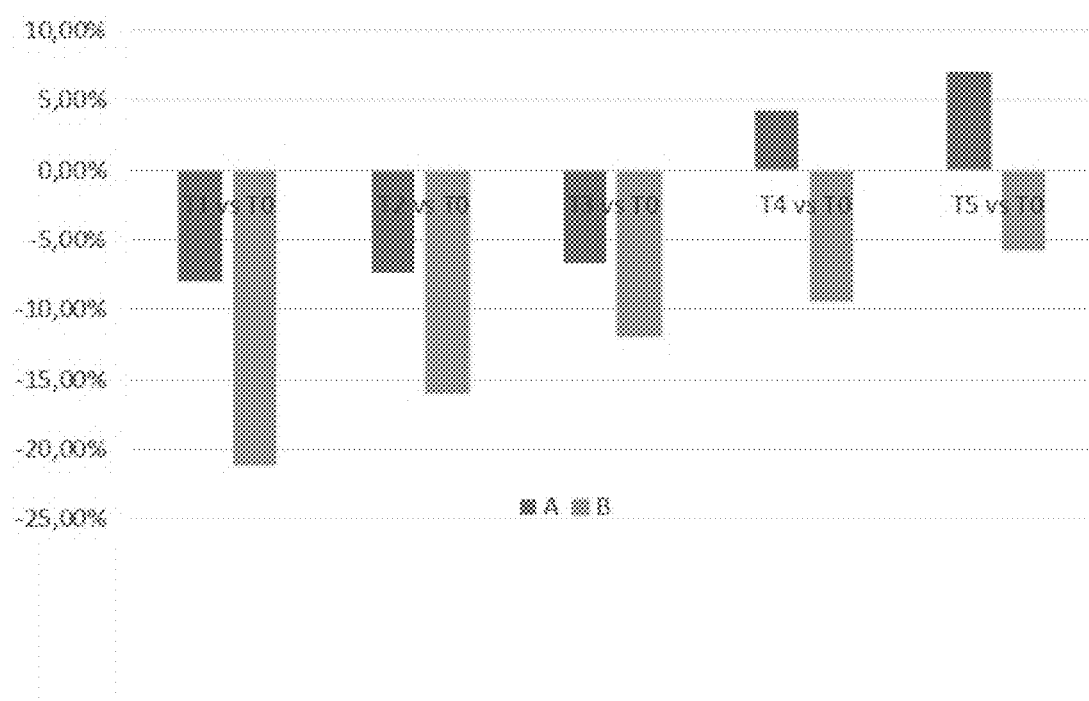
FIG. 17. Measurements with the Tewameter® were performed at T0, T1, T2, T3, T4 and T5. Product A (grey) is a basic cream formula containing no active ingredient but glycerin (placebo). Product B (pink) is a basic cream formulation containing 0.5% Black spruce bark extract. Results are expressed as mean percentage difference of the measured parameters at T1, T2, T3, T4 and T5 in comparison to the parameters measured at T0 and statistical evaluation was performed in order to evaluate the significance of the observed differences. Improving effect on the skin barrier is indicated by a decrease in percentage.

Protector effect of Black spruce bark extract is presented in FIG. 17, indicating a protecting effect by a marked decrease in water lost. Under the experimental conditions of this study, the protective effect of Black spruce bark extract is shown by a decrease skin water loss.

CONCLUSION

We demonstrated that crude bark extracts, without any procedure of fractionation and purification, exhibit anti-aging effectiveness which indicates that this extract can find applications as cosmetic products, not only to prevent damage provoked by oxidative stress in the human organism, but also as a specific inhibitors of skin degradation enzymes and as a stimulator of healthy skin components.

Finally, we anticipate a real potential for the application of Black spruce bark extract following the integration of the extraction units into the existing forest industry mills, which will be thus transformed into biorefineries of the future.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

All patents, patent applications and publications mentioned in this specification are herein incorporated by reference to the same extent as if each independent patent, patent application or publication was specifically and individually indicated to be incorporated by reference.

REFERENCES

Moure, A., Cruz, J. M., Franco, D., Manuel Domínguez, J., Sineiro, J., Domínguez, H., Núñez, M. J., Carlos Parajó, J., 2001. Natural antioxidants from residual sources. Food Chem. 72, 145-171.

Stevanovic, T., Diouf, P. N., Garcia-Perez, M.-E., 2009. Bioactive polyphenols from healthy foods and forest biomass. Curr. Nutr. Food Sci. 5, 264-295.

The invention claimed is:

1. A method for inhibiting skin aging in a mammal, comprising contacting said skin with an enzyme-inhibiting concentration of a solvent extract from *Acer rubrum* tree bark or from *Picea mariana* tree bark, wherein the enzyme is selected from: elastase and collagenase.

2. The method of claim 1, wherein the solvent is water or ethanol, or a mixture thereof.

3. The method of claim 1, wherein the aging of the skin is associated with: wrinkles, loss of skin hydration, or loss of skin elasticity.

4. The method of claim 1, wherein said enzyme is inhibited to greater than about 10%, 15% or 20% by the extract, when tested under in vitro conditions.

5. The method of claim 1, wherein the extract is admixed with a physiologically-acceptable carrier, and formulated as a dermatological formulation for topical administration.

6. The method of claim 5, wherein the carrier is glycerin.

7. The method of claim 5, wherein the dermatological formulation is a cosmetic.

8. The method of claim 5, wherein the dermatological formulation comprises about 1% to about 10% by weight of dried extract.

9. The method of claim 7, wherein the formulation is selected from a: cream, gel, lotion, and serum.

10. The method of claim 1, wherein the composition comprises a mixture of *Acer rubrum* bark extract and *Picea mariana* bark extract, in admixture with a physiologically-acceptable carrier.

11. The method of claim 10, wherein the carrier is glycerin.

12. A method of treating skin aging in a mammal, comprising contacting said skin with a skin-component synthesis-enhancing amount of a red maple bark solvent extract, wherein the skin-component is selected from: elastin, collagen and involucrin.

13. The method of claim 12, wherein the solvent is water or ethanol, or a mixture thereof.

14. The method of claim 12, for treating wrinkles on human skin.

15. The method of claim 12, for maintaining or increasing elasticity of human skin.

16. The method of claim 12, for maintaining or increasing firmness of human skin.

17. The method of claim 12, wherein the extract is admixed with a physiologically-acceptable carrier, and formulated as a dermatological formulation for topical administration.

18. The method of claim 17, wherein the dermatological formulation is a cosmetic.

19. The method according to claim 17, wherein the extract is present in an amount between 0.05% and 20% w/w in the dermatological formulation.

20. The method of claim 18, wherein the dermatological formulation is selected from a: cream, gel, lotion, and serum.

* * * * *